US010362943B2

(12) United States Patent
Dumont et al.

(10) Patent No.: US 10,362,943 B2
(45) Date of Patent: Jul. 30, 2019

(54) DYNAMIC OVERLAY OF ANATOMY FROM ANGIOGRAPHY TO FLUOROSCOPY

(71) Applicant: Siemens Healthcare GmbH, Erlangen (DE)

(72) Inventors: Guillaume Dumont, Plainsboro, NJ (US); Peng Wang, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1273 days.

(21) Appl. No.: 14/444,120

(22) Filed: Jul. 28, 2014

(65) Prior Publication Data

US 2015/0087972 A1    Mar. 26, 2015

Related U.S. Application Data

(60) Provisional application No. 61/880,346, filed on Sep. 20, 2013.

(51) Int. Cl.
*A61B 5/00* (2006.01)
*A61B 5/0402* (2006.01)

(52) U.S. Cl.
CPC .......... *A61B 5/0071* (2013.01); *A61B 5/0402* (2013.01); *A61B 5/7285* (2013.01); *A61B 2576/023* (2013.01)

(58) Field of Classification Search
CPC ............ A61B 2576/023; A61B 5/0071; A61B 5/0402; A61B 5/7285
See application file for complete search history.

(56) References Cited

U.S. PATENT DOCUMENTS

| 2012/0059253 | A1  | 3/2012 | Wang et al. |
| 2012/0070046 | A1  | 3/2012 | Wu et al. |
| 2012/0089003 | A1* | 4/2012 | Ostermeier ............ A61B 6/032 600/407 |
| 2012/0093397 | A1  | 4/2012 | Wang et al. |
| 2012/0238866 | A1  | 9/2012 | Wang et al. |
| 2013/0011030 | A1  | 1/2013 | Tzoumas et al. |
| 2016/0196666 | A1* | 7/2016 | Venkatraghavan ..... G06T 7/254 382/130 |

OTHER PUBLICATIONS

P.B. Shah, "Management of Coronary Chronic Total Occlusion," Circulation; 123, pp. 1780-1784, 2011.
P. Wang, et al., "Robust Guidewire Tracking in Fluoroscopy," IEEE International Conference on Computer Vision and Pattern Recognition (CVPR), 2009.
G. Welch, et al., "An Introduction to the Kalman Filter," TR 95-041, 2006.

* cited by examiner

Primary Examiner — Michael T Rozanski

(57) ABSTRACT

An overlay of anatomy is created for a fluoroscopy image. Anatomy detected in angiographic images is used to locate anatomy in the fluoroscopy image. For each cardiac phase, the anatomy is detected multiple times from different cardiac cycles using angiographic images. The fluoroscopic overlay for each cardiac phase is formed from a combination of angiographic candidates fit from the different cardiac cycles to the fluoroscopic image. To further enhance the combination, prediction of the anatomy position from one phase to the next phase is used.

14 Claims, 6 Drawing Sheets

DYNAMIC OVERLAY OF ANATOMY FROM ANGIOGRAPHY TO FLUOROSCOPY

RELATED APPLICATIONS

The present patent document claims the benefit of the filing date under 35 U.S.C. § 119(e) of Provisional U.S. Patent Application Ser. No. 61/880,346, filed Sep. 20, 2013, which is hereby incorporated by reference.

BACKGROUND

The present embodiments relate to fluoroscopy. 2D X-ray fluoroscopy is routinely used for vascular interventions and for cardiac catheterization. For example, coronary artery chronic total occlusion (CTO) is a heart disease that causes a decrease in the blood flow of concerned patients. One of the procedures available to treat this disease is a percutaneous coronary intervention (PCI), which relies on the insertion of a catheter through the obstructed artery to release the occlusion.

An angiography is used to determine the severity of the CTO before an intervention to estimate if a PCI may be performed safely. Contrast agent is administered during angiography to make the coronary vessels visible on the X-ray images. Fluoroscopy is used for real-time monitoring of the procedure and catheter location visualization. During the intervention, the practitioner tracks the progress of the catheter in the arteries. However, 2D fluoroscopic images lack detailed anatomical information due to the X-rays limitations in distinguishing among soft tissues. Anatomy may be more visible with injection of contrast agents, but using extra contrast agent during the procedure may subject the patient to harmful side effects.

In order to augment the doctor's visualization of the body anatomy during the intervention, an overlay of computer detected anatomy may be provided on the fluoroscopic image. Such an overlay may help the practitioner localize the vessel structures during the surgery procedure with less contrast agent. However, accurately determining the anatomy location in the fluoroscopic image for the overlay may be difficult and/or inexact.

BRIEF SUMMARY

By way of introduction, the preferred embodiments described below include methods, systems, instructions, and computer readable media for generating an overlay of anatomy in a fluoroscopy image. Anatomy detected in angiographic images is used to locate anatomy in the fluoroscopy image. For each cardiac phase, the anatomy is detected multiple times from different cardiac cycles using angiographic images. The fluoroscopic overlay for each cardiac phase is formed from a combination of angiographic candidates fit from the different cardiac cycles to the fluoroscopic image. To further enhance the combination, prediction of the anatomy position from one phase to the next phase is used.

In a first aspect, a method is provided for generating an overlay of anatomy in a fluoroscopy image. An angiograph acquires an angiograph image representing the anatomy of a patient at a first phase of a first cardiac cycle of the patient. A fluoroscope acquires a fluoroscopic image representing the anatomy of the patient at the first phase of a second cardiac cycle of the patient. A processor determines a shape of the anatomy in the fluoroscopic image from the angiograph image. The overlay of the anatomy is generated as a graphic on the fluoroscopic image. The overlay being a function of the shape determined from the angiographic image.

In a second aspect, a non-transitory computer readable storage medium has stored therein data representing instructions executable by a programmed processor for generating an overlay of anatomy in a fluoroscopy image. The storage medium includes instructions for modeling a location of the anatomy of a patient in each of a plurality of frames of angiographic data over two or more heart cycles; for a first phase of the heart cycles, combining the locations from the different heart cycles, wherein the combining includes using a prediction of the location associated with a second phase, the combining resulting in combined location of the anatomy; and generating the overlay of the anatomy in the fluoroscopy image, the overlay being at the combined location.

In a third aspect, a system is provided for generating an overlay of anatomy in a fluoroscopy image. An angiography system is configured to acquire a sequence of angiographic data representing a vessel of a patient at different phases in multiple heart cycles. A fluoroscopy system is configured to acquire fluoroscopic data representing the vessel of the patient at a first one of the phases. A processor is configured to fit a first shape model of the vessel at the first phase in the angiographic data of each of the multiple heart cycles to the fluoroscopic data, to predict a second shape model associated with a second one of the different phases, to combine the fit shape models from the different heart cycles as a function of the second shape model, and to generate the overlay of the vessel on a fluoroscopic image from the fluoroscopic data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

During surgical interventions, angiography and fluoroscopy are used to visualize anatomical shapes and medical devices in real time. When no or little contrast agent is injected during fluoroscopy, some anatomical structures may not be visible or very visible in the X-ray images. A preoperative static overlay of these structures may sometimes be inaccurate due to the environmental motions involved. Similarly, detecting anatomy for highlighting in a fluoroscopic image may be inaccurate.

Dynamic overlay of anatomy modeled from multi-cycle angiography to fluoroscopy is provided. A dynamic overlay or overlay that changes over time with the heart and/or breathing cycles of anatomical structures on fluoroscopy X-ray images is provided. The dynamic overlay of the anatomy is based on fusing candidate overlays from a multi-cycle angiography sequence and prediction. Candidate overlays of these anatomical structures on the fluoroscopy images are created based on angiographic anatomy from different cycles. By tracking the medical devices and anatomical structures during only a few heart cycles in an angiography sequence, a model for their motion during the intervention is created. The position of anatomy across several frames in fluoroscopy imaging is predicted using the model for motion. By using the prediction model and the candidate overlays, the dynamic overlay of the anatomical structures on the fluoroscopy images is provided to assist the practitioners during surgical interventions.

Figure 1:
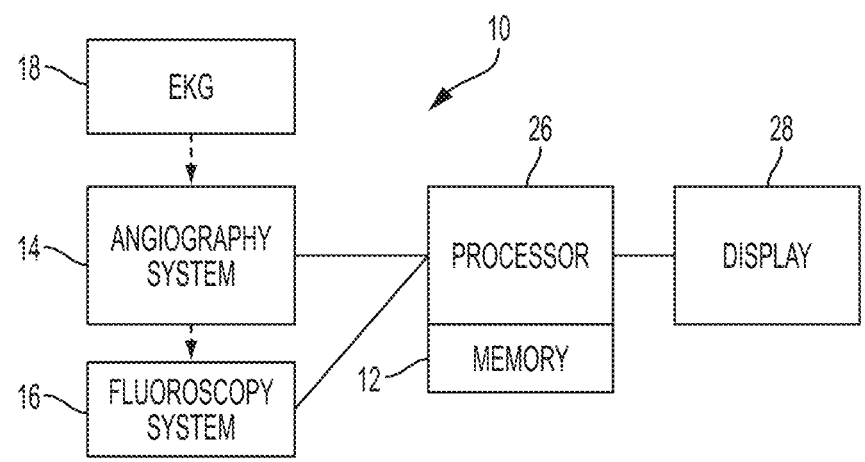
FIG. 1 is a block diagram of one embodiment of a system for generating an overlay of anatomy in a fluoroscopy image.

FIG. 1 shows a system 10 for generating an overlay of anatomy in a fluoroscopy image. The system 10 includes a memory 12, an angiography system 14, a fluoroscopy system 16, an electrocardiogram (EKG) 18, a processor 26, and a display 28. Additional, different, or fewer components may be provided. For example, a network or network connection is provided, such as for networking with a medical imaging network or data archival system. As another example, a preoperative imaging system, such as a computed tomography or magnetic resonance imaging system, is provided with or as an alternative to the memory 12. In another example, a user interface is provided. In yet another example, the angiography and fluoroscopy systems 14,16 are a same x-ray system.

The processor 26 and display 28 are part of a medical imaging system, such as the fluoroscopy system 16, angiography system 14, or other system. Alternatively, the processor 26 and display 28 are part of an archival and/or image processing system, such as associated with a medical records database workstation or server. In other embodiments, the processor 26 and display 28 are a personal computer, such as desktop or laptop, a workstation, a server, a network, or combinations thereof. The processor 26, display 28, and memory 12 may be provided without other components for implementing the method.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data or video information.

The memory 12 is part of an imaging system, part of a computer associated with the processor 26, part of a database, part of another system, a picture archival memory, or a standalone device.

The memory 12 stores data representing a region, at different times, of a patient. The region is a two or three-dimensional region. The region is of any part of the patient, such as a region within the chest, abdomen, leg, head, arm, or combinations thereof. The data is angiographic, fluoroscopic, and/or other image data. The data includes information representing a catheter while in the region and vessel. The data may represent the vessel without the catheter.

The data is from scanning the region by any medical imaging modality. Any type of data may be used, such as medical image data (e.g., ultrasound, x-ray, computed tomography (CT), magnetic resonance imaging (MRI), or positron emission tomography). In one embodiment, the data representing the patient volume is angiography data and fluoroscopy data. The data represents the patient prior to or during treatment. For example, angiography is acquired prior to catheterization or prior to use of a catheter to remediate a blocked vessel. The fluoroscopy data is acquired during a catheterization and during remediation.

Image data is data that can be used to generate an image, pixels values to be displayed, pixel values that were displayed, or other frames of data representing the region of the patient at a given time. The image data may be frames of DICOM data or frames of data generated along any portion of a data processing path of an imaging system. A sequence of frames of data is acquired, such as acquiring angiography images over two or more heart cycles at any frame rate (e.g., 10-20 frames per second) and fluoroscopy images over at least one cycle at the same or different frame rate. The fluoroscopy and angiography frames represent the region at the same or different phases of the heart cycle.

As an alternative to storing image data, the memory 12 stores candidate locations for the position of the anatomy, catheter, and/or other medical device. The image data is transferred to the processor 26 without storage in the memory 12 or with storage in another memory.

The memory 12 or other memory is alternatively or additionally a computer readable storage medium storing data representing instructions executable by the programmed processor 26 for generating an overlay of anatomy in a fluoroscopy image. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The EKG 18 is an EKG system with one or more electrodes. While shown by dashed lines connected to both the fluoroscopy system 16 and the angiography system 14, separate EKG systems may be used for each. As an alternative to a discrete EKG system, one or both imaging systems 14, 16 may have built-in EKG sensors.

The EKG 18 acquires a signal or signals representing the electrical activity of the heart captured over time. One or more electrodes connected to the patient's skin are used in one embodiment. The EKG 18 indicates the timing of each image capture, such as the phase and heart cycle.

Manual or automatic heart cycle detection may be used. A user may indicate a heart cycle number for any given image. Alternatively, the processor 26 or other processor determines the number of heart cycles. Similarly, phase for a given image is determined automatically or manually. The EKG trace is shown for manual and/or automatic phase detection. For automatic phase detection, the EKG trace or detected points in the EKG trace are used.

The x-ray angiography X x-ray detector on a C-arm or other robotic mechanism for positioning relative to the patient. The angiography system 14 includes position sensors for determining changes in position of the X-ray source and/or detector. In alternative embodiments, the angiography system 14 is a CT angiography or MR angiography system.

For angiography imaging, a contrast agent (e.g., iodine) may be injected into a patient. The contrast agent provides a detectable response to X-rays. By flowing through the circulatory system, the contrast agent may provide detectable response highlighting the circulatory system, such as the vessels (veins or arteries) and/or heart. By transmitting X-rays through the patient to the detector, a projection image is provided. Any tissue, bone, catheter, and contrast agent along the path of travel of the X-ray beam interacts with the X-rays, causing a detectable difference in intensity at the detector. Since each pixel or location of the detector represents an accumulation of responses along the path of travel, the angiography image is a projection image of the region.

An angiographic image may be generated with or without response from the catheter and/or other medical device. For example, during intervention, the catheter may be positioned within the patient. One or more angiographic images are generated in real-time just before or during the interventional procedure. Contrast agent is injected into the patient, and a sequence of angiography images over multiple (e.g., two, three, or more) heart cycles is acquired. The angiographic representation of the vessel, catheter, other medical device, and/or other anatomy in the patient is provided for different phases in each of the multiple heart cycles.

Figure 2:
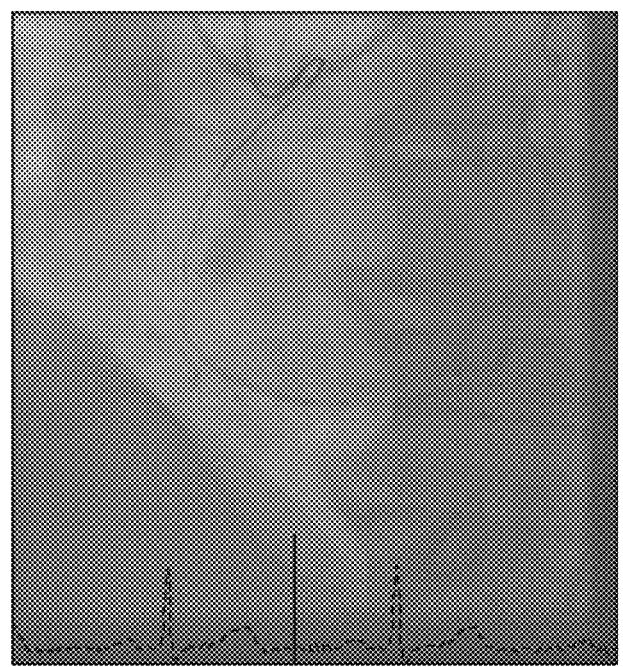
FIG. 2 is an example fluoroscopy image with an EKG overlay.

The frames of the sequence are acquired with EKG labeling indicating the phase with or without indication of a heart cycle number. Interpolation may be used to associate detected phases of the heart cycle with the phase at which any given image is acquired. FIG. 2 shows an example angiography image with an overlaid EKG trace where the vertical straight line shows the phase within a given heart cycle at which the frame of angiography data was acquired.

The fluoroscopy system 16 is any now known or later developed fluoroscopy system. In one embodiment, the fluoroscopy system 16 is the same system as the angiography system 14, but may be a separate system. The fluoroscopy system 16 includes an x-ray source and detector separated by a region into which the patient is positioned. Using a C-arm or other supporting structure, X-rays passing through the patent are detected. Unlike angiography, the fluoroscopy images may not include contrast agent. Thus, the anatomy may be less visible.

By transmitting X-rays through the patient to the detector, a projection image is provided. Any tissue, bone, catheter, other medical device, and contrast agent along the path of travel of the X-ray beam interacts with the X-rays, causing a detectable difference in intensity at the detector. Since each pixel or location of the detector represents an accumulation of responses along the path of travel, the fluoroscopy image is a projection image of the region.

The fluoroscopy image is generated with response from the catheter. For example, during intervention, the catheter may be positioned within the patient. One or more fluoroscopy images are generated in real-time during the interventional procedure and after confirmation of occlusion using angiography. A single fluoroscopy image is acquired, or a sequence of fluoroscopy images over multiple (e.g., three or more) heart cycles is acquired. The fluoroscopy image represents the vessel, catheter, other medical device, and/or other anatomy in the patient for one or different phases in any one or multiple heart cycles.

The frames of the fluoroscopy sequence are acquired with EKG labeling indicating the phase with or without indicating a heart cycle number. Interpolation may be used to associate detected phases of the heart cycle with the phase at which any given image is acquired.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for generating a dynamic overlay for fluoroscopy from angiography detected anatomy. The processor 26 is a single device or multiple devices operating in serial, parallel, or separately. The processor 26 may be a main processor of a computer, such as a laptop or desktop computer, or may be a processor for handling some tasks in a larger system, such as in an imaging system. The processor 26 is configured by instructions, design, hardware, and/or software to be able to perform the acts discussed herein.

Figure 3:
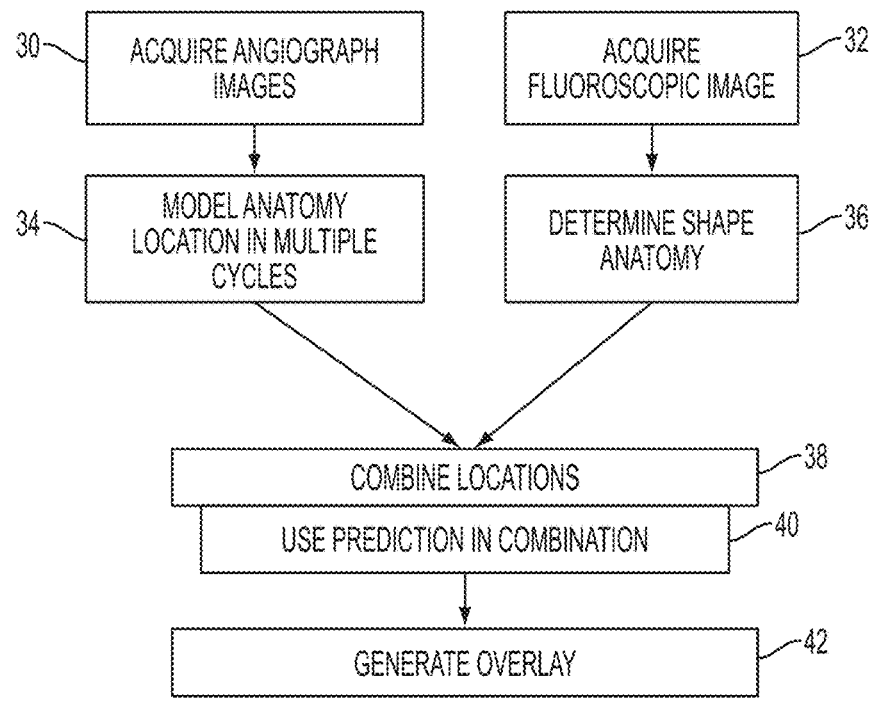
FIG. 3 is a flow chart diagram of one embodiment of a method for generating an overlay of anatomy in a fluoroscopy image.

FIG. 3 shows an example method implemented, at least in part, by the processor 26. As compared to the specifics of FIG. 3, the operation of the processor 26 is now described in general. The processor 26 uses angiography images to find anatomy appropriate for a given phase. The overlay for a fluoroscopy image for that phase is determined, at least in part, from the anatomy in the angiography images. In one example embodiment, the processor 26 is configured to create candidate locations for anatomy in a given fluoroscopic image from the anatomy in each of multiple angiography images from different heart cycles. The processor 26 fits a shape model of the vessel at the given phase in the angiographic data of each of the multiple heart cycles to the fluoroscopic data or model from the fluoroscopy data.

Further information is provided by the processor 26 as the processor 26 predicts another shape model associated with a different phase. For example, the prediction from a different phase may be of the shape of the anatomy at the given phase of the fluoroscopic image. As another example, the prediction may be used in Kalman filtering. The processor 26 is configured to combine the fit shape models from the different heart cycles as a function of the predicted shape model, such as by including the predicted model in an averaging of the candidates or including in the Kalman filtering.

The overlay of the vessel is generated by the processor 26 on a fluoroscopic image. For generating the dynamic overlay, the processor 26 repeats the generation of the overlay for fluoroscopy images at different phases.

The display 28 is a monitor, LCD, projector, plasma display, CRT, printer, or other now known or later developed devise for outputting visual information. The display 28 receives images, graphics, or other information from the processor 26, memory 12, angiography system 14, or fluoroscopy system 16.

One or more fluoroscopy images representing a catheter position relative to a patient region are displayed. The location of the medical device (e.g., catheter) is or is not highlighted, marked by a graphic, or otherwise indicated on the image. For example, an image includes fluoroscopic information showing the location of a catheter. Where a sequence of images is displayed, the location of each medical device is shown in each of the images.

The fluoroscopy image also includes anatomy of a vessel associated with occlusion and/or the catheter. The anatomy is highlighted on the fluoroscopy image using an overlay. The overlay is a graphic, pixel coloring, and/or other indicator of the anatomy more than mere display of the fluoroscopy intensity values. Since the anatomy is less visible in fluoroscopy, the anatomy is highlighted by the overlay to assist the physician in guiding and/or using the medical device.

FIG. 3 shows a method for generating an overlay of anatomy in a fluoroscopy image. The method is implemented by the system 10 of FIG. 1 or another system. The acts are performed in the order shown or other orders. Additional, different, or fewer acts may be provided. For example, the output act 42 is not provided, but instead the determined anatomy location is used to register medical scans. As another example, the prediction of act 40 is not used. In yet another example, acts 30-36 are not provided, but the anatomy shape models are given as an input for combination in act 38.

In act 30, a sequence of angiograph images is acquired. The acquisition is from a memory, such as loading DICOM images. Alternatively, the acquisition is by operation of an angiograph scanner.

One frame of data representing anatomy of a patient with an inserted catheter and/or other medical device is acquired. The anatomy, such as one or more vessels, include contrast agent. As a result, the intensity for locations associated with the vessel is higher than for surrounding soft tissue. Similarly, the intensity for the metal or other denser medical instrument materials is higher than for surrounding soft tissue.

The frame of data represents the patient at a phase of a cardiac cycle. The EKG information is used to determine the cardiac cycle as well as the phase. The phase is based on a trigger point in the EKG, a time from a start of the heart cycle, or a proportional timing relative to the entire heart cycle.

A plurality of these frames of angiography data is acquired. The frames of angiography data are acquired prior to intervention. For example, the frames are acquired once a catheter is positioned within the patient for the intervention but prior to removing the obstruction. Once the catheter is positioned, contrast agent is injected into the circulatory system of the patient. The frames are acquired as the contrast agent arrives or after arrival through to the contrast agent leaving or before wash out. In alternative embodiments, the frames are acquired as part of obstruction confirmation prior to insertion of the medical instrument, such as the catheter.

The frames represent the region of the patient at different phases throughout a cycle, such as acquiring 10-20 frames in one heart cycle. EKG timing information, such as the EKG trace, is acquired with or used to encode phase or timing information for each of the frames of the sequence. The sequence extends over multiple cardiac cycles. Frames of angiography data representing the patient at different phases through multiple heart cycles (e.g., 2, 3, 4 or more cycles) are obtained. The frames from the different cardiac cycles may represent the same or similar phases. For example, the frames for one cycle may be shifted within the cycle to represent different phases within 10% of the cycle of phases represented in a different cycle.

In one embodiment, the angiograph images or frames of different heart cycles are interpolated to common phases. The phases for which angiograph images are obtained for one cycle may be offset from the phases for another cycle. The number of phases considered in a heart cycle is determined by the data availability or is predetermined. For example, if the number of phases is higher than the maximum number of frames present during a heart cycle in angiography, some phases might not have any data. By selecting the maximum number of frames present during a heart cycle, failure to provide the predetermined number is avoided. Furthermore, obtaining as many phases as possible is important to reduce interpolation approximations when registering motion to a phase in prediction.

In order for the frames of angiographic data to represent the same times within the heart cycle despite being offset between heart cycles, the frames throughout each heart cycle are interpolated to the same phases. In one embodiment, the phases for a selected (e.g., initial) heart cycle are used. The frames for other heart cycles are interpolated to represent the same phases as for the selected heart cycle. In the X-ray sequences, the number of frames available in each cardiac cycle is not always the same. By registering the frames to a cardiac phase using interpolation, common phasing is provided. In one embodiment, a weighted interpolation is used. The weights are based on the temporal distance of the frame from the desired phase. The two frames closest to the desired phase are weighted and averaged. Algorithm 1 represents this approach:

```
Function Register (c,p)
  nPhases←number of phases
  nFrames←cycle size (c)
  index←nFrames/nPhases×p
  previous frame←get frame (c, ⌊index⌋)
  next frame←get frame (c, ⌈index⌉)
  f₁←previous frame
  f₂←next frame
  w₁←index-⌊index⌋ ▶ weight of f₁
  W₂←1-w1 ▶ weight of f₂
  f=w₁×f₂+w₂×f₂ ▶ interpolation
  register (p,f) ▶ register interpolated frame
end function
``` where c is the cardiac cycle index, p is a phase given as an EKG time offset, and nPhases indicates the number of phases in a cardiac cycle being used.

Other approaches may be used, such as selecting the temporally closest frame to represent the phase. In yet other embodiments, interpolation or shifting to have common phases represented throughout the different cycles is not performed.

In act 32, one or more fluoroscope images are acquired. The acquisition is from a memory, such as loading DICOM images. Alternatively, the acquisition is by operation of a fluoroscope.

One frame of data representing anatomy of a patient with an inserted catheter and/or other medical device is acquired. The anatomy, such as one or more vessels, may or may not include contrast agent. Typically, the fluoroscope image is acquired for a time in which the region of the patient is free of or has little contrast agent. As a result, the intensity for locations associated with the vessel is similar to or blends with the intensities for surrounding soft tissue. The intensity for the metal or other denser medical instrument materials is higher than for surrounding soft tissue.

The frame of data represents the patient at a phase of a cardiac cycle. The EKG information is used to determine the cardiac cycle as well as the phase. The phase is based on a trigger point in the EKG, a time from a start of the heart cycle, or a proportional timing relative to the entire heart cycle. The cardiac cycle is a same one or different one for which angiographic information is acquired. The phase is a same one, similar, or different phase than phases for which angiography frames are acquired or interpolated. The acquisition triggering or timing for the fluoroscopy and angiography may be unsynchronized or may be synchronized.

In one embodiment, a plurality of the frames of fluoroscopy data is acquired. The frames represent the region of the patient at different phases throughout a cycle, such as acquiring 10-20 frames in one heart cycle, or throughout many cycles. EKG timing information, such as the EKG trace, is acquired with or used to encode phase or timing information for each of the frames of the sequence. The sequence extends over a portion of one or multiple cardiac cycles. The frames from the different cardiac cycles may represent the same or similar phases.

The frames of fluoroscopy data are acquired prior to and/or during intervention. For example, the frames are acquired to guide placement of a catheter within the patient for the intervention. During the obstruction remediation, frames of fluoroscopy data are acquired to monitor the position of the medical instrument relative to the anatomy.

In act 34, the location of anatomy of the patient and/or medical devices is modeled in the frames of angiographic data. The shape, such as the vessel, is modeled in each or some of the angiographic images throughout the sequence. For example, a curve representing the vessel is fit to the angiographic data for different frames throughout multiple cycles. The model showing the location of the anatomy is provided for the different phases through the different cycles.

In one embodiment, the location of the anatomy is modeled as a cubic spline. Other curve representations may be used. Models of location that are other shapes, such as area or volume shapes, may be used. For example, the vessel locations are segmented.

The medical device or devices may also be modeled. The same or different model may be used. For example, the catheter is modeled as a segmented or separate part of the cubic spline of the vessel. As another example, the catheter tip, guidewire tip, or other points are modeled.

Figure 4:
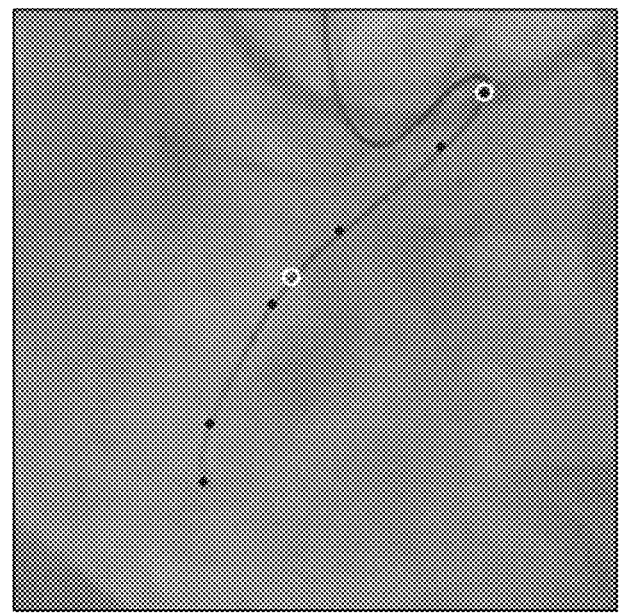
FIG. 4 is an example angiography image with a shape model.

In one embodiment, the catheter and the coronary vessels are modeled or tracked through the sequence. The tracking is performed by independent detection in each frame or by correlation or other dependent detection from frame to frame. For example and as represented in FIG. 4, the catheter tip, guidewire body, micro-catheter tip (lower circle), guidewire tip, and the coronary vessel seen on the angiography sequence after contrast dye injection are modeled. Additional, different or fewer parts may be modeled depending on the detection technique. The catheter and micro-catheter tip are modeled using points whereas the guidewire is modeled using a cubic spline, but other modeling using points, curves, or areas for any of the parts may be used. The coronary vessels' branches are segmented and modeled using cubic splines.

Figure 5:
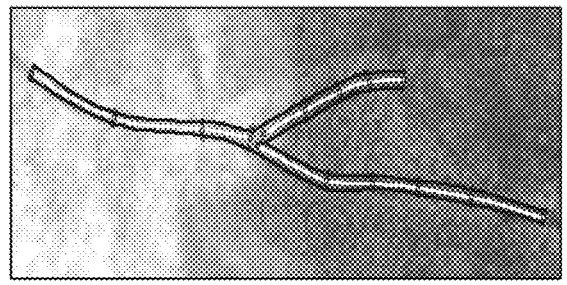
FIG. 5 shows example splines for a vessel in angiography.

The model of the locations of the anatomy is created manually or automatically. For manual, a user indicates the locations of the anatomy in the sequence of images. For automatic, semi or fully automatic approaches may be used. The user may indicate one or more locations along the anatomy and the processor determine other locations. The processor may apply image processing to identify all locations without location input for a given image from the user. FIG. 5 is an example of a segmented vessel using manual annotations on an angiography frame. The center and edges of the vessel are modeled as cubic splines with each branch being separately modeled.

In one example embodiment, one or more detectors or classifiers are applied. The same or different detector is applied for different medical devices and/or anatomy where there are multiple devices and/or anatomy being tracked or detected. In one approach, the detectors identify different candidate positions of the shape models. The detected positions are candidate locations in a given frame. The detected positions may or may not be the actual location. Any now known or later developed detection may have been used to provide the candidate locations. In one example, learning-based detectors are used for object detection and tracking. The learning-based classifier is trained from a set of off-line collected data, including both object samples (positive) and non-object samples (negative), to learn the decision boundary that separates the positive from negative samples. One example learning-based classifier is the probabilistic boosting tree (PBT). The classifiers are trained from any one or more types of features, such as using Haar features. The detectors may be constructed in a hierarchical way. Each detection candidate for each medical device and/or anatomy may be associated with a confidence score that is provided by PBT. Filtering, other selection, other classifiers, or other processes may be used to detect.

In other embodiments, the detection is by filtering to enhance linear, curve, or line structures. Gradient-based, pattern matching, region growing or other detection may be used to determine the location or locations of anatomy or medical devices in each frame.

Where multiple candidates are found, the number of the input candidates may be pruned by checking validity. For example, the most likely ten or twenty candidates are used in each frame. As another example, a criterion may be applied to prune the number of candidates based on the criterion rather than limiting to a certain number of candidates. In one embodiment for a catheter candidates, the criteria compares between frames. The geodesic distance between each candidate and a reference location is used.

A processor identifies one location of the anatomy or medical device in each of the frames. The location is identified from among the candidate locations for the respective frame. Rather than determine a new location, one of the candidate locations is selected as the detected position of the device. Such selection occurs in each of the frames. In one embodiment, the identification for a frame is based on the candidate locations in the given frame and candidate locations in other frames. The identification is also based on the motion and/or locations of other anatomy or devices. Alternatively, just the candidate locations without guide wire motion are used. Other inputs may be used. In one example, the identification is performed by inferring the maximum of a probability function. The inference problem is formulated as an optimization problem. The candidate locations from all, a windowed subset, or other collection of multiple frames are used to optimize the probability of each candidate. The candidate with the optimum location is identified. In one embodiment, a graphical model is constructed and the maximum a posterior probability (MAP) approach is employed to find the inference results. Other detection may be used, such as detecting a single location without use of candidates.

In act 36, a shape of the anatomy and/or medical devices is determined in the fluoroscopic image or images. The processor, the user, or the processor and user model the locations of the anatomy in each of the frames of fluoroscopic data. The same or different detection as used for the frames of angiographic data is used. Similarly, the medical device or medical devices may be modeled. For example, anatomy and device shape models are found. Because the fluoroscopy images are overlaid in real time, a tracking method or automated detection by a processor is used.

In one embodiment, the same parts of the medical devices, medical devices, and anatomy are determined as for the angiograph images. For example, the catheter tip, guidewire body, micro-catheter tip, guidewire tip, the microcatheter, and the coronary vessels are located. The catheter and micro-catheter tip are modeled using points whereas the guidewire is modeled using a cubic spline. The coronary vessels' branches are segmented using cubic splines.

Since contrast agents may not highlight the anatomy in the frames of fluoroscopy data, the detection of the anatomy in the fluoroscopy data may be unreliable. As a result, the model of the detected anatomy is not used for generating the overlay. Instead, the shape models of the angiography images with or without predictions from other phases are used to generate the overlay through the combination of act 38.

In act 38, the modeled locations from different frames of angiographic data are combined to find the location for the dynamic overlay. Locations from angiography are used for finding the location of anatomy in the fluoroscopy. Multiple candidates for the location of anatomy in a given frame of fluoroscopic data are provided from the models of multiple frames of angiography data. The models used from the angiography are for the same phase, but from different cycles. For example, a frame of fluoroscopic data represents the patient at one phase of the heart cycle. The models from different cycles but that same one phase in the angiography sequence are used as candidates. As a frame of fluoroscopic data for a new (different) phase is acquired, multiple candidates of modeled locations for that new phase from the multiple cycles are selected from the angiographic sequence.

During angiography, the coronary vessels are only visible during a few heart cycles after the contrast agent is injected by the practitioner. Each one of these cycles is used to determine a candidate overlay for each cardiac phase. To create an overlay that dynamically adapts to any environmental change (i.e. breathing motion, movement of the patient, etc. . . . ), the shape models from angiography are fit to the shape model from fluoroscopy. Because of breathing motion, noise is added to the vessels' position in angiography. Therefore, gathering multiple noisy overlay candidates may help reduce this noise. In one embodiment, the location of coronary vessels on the fluoroscopy image is found based on fusing information from a multi-cycle angiography sequence. The shape models for the medical devices may be used for scaling and/or to assist in fitting the anatomy shape models.

The candidates for the location of anatomy are refined by fitting the models of the angiographic information to the model of the fluoroscopic information. Shape models from multiple cycles in angiography are fit to fluoroscopy to create the candidates of the anatomy location in the fluoroscopy. For example, three models for a given phase are available from the angiography sequence being over three cardiac cycles. Each of those three models is separately fitted to the model determined from the frame of fluoroscopic data for that same or similar phase.

To fit the models from angiography to the model from fluoroscopy, the translation, rotation, and/or scale to transform from angiography to fluoroscopy is determined. Any fitting may be used, such as rigid or affine. In one embodiment, the fitting is rigid in order to preserve the geometry of the vessel after transformation. An affine model may be too sensitive to imprecision during the microcatheter tip tracking or other position determination. For example, the microcatheter tip is used as one of two stationary points in the vessel to resample in scaling the models. Any wrong tracking or detection of the tip may cause an incorrect scaling factor to be detected.

Figure 6:
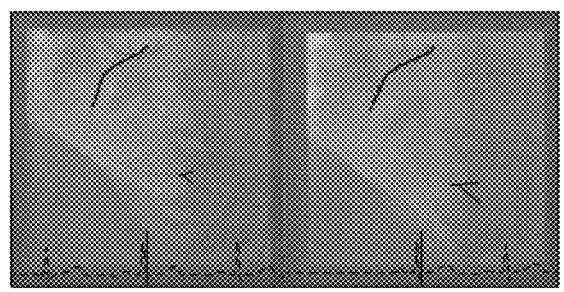
FIG. 6 shows an angiography image with a highlighted vessel and the fitting of the vessel to the fluoroscopy image.

The fitting may an affine model with a reduced domain for the scaling factor s and/or other fitting characteristics, making the fitting semi-rigid. FIG. 6 shows the preservation of the vessel's geometry after fitting. The left side is an annotated angiography image, and the right side shows angiography annotations fitted to the determined locations of the fluoroscopy image. The fitting may be represented as:

$$\begin{matrix} y_1 \\ y_2 \end{matrix} = s \cdot \begin{bmatrix} \cos\theta & -\sin\theta \\ \sin\theta & \cos\theta \end{bmatrix} \cdot \begin{matrix} x_1 \\ x_2 \end{matrix} + \begin{matrix} S_1 \\ S_2 \end{matrix} \qquad (1)$$

where the indices 1 and 2 are coordinates, x is the vectors of points on a spline, and y are the vectors of target points on the spline after transformation, s is a scale factor, S are translation offsets, and $\theta$ is a rotation.

Equation 1 represents an affine transformation for fitting. On some frames, the shape of the guidewire may vary a lot due to the breathing motion, making the fitting between angiography and fluoroscopy inaccurate. Fitting two differently shaped guidewires affects the rotation factor significantly and causes jumps in the vessel overlay. In one approach, the domain of the rigid transformation is restrained to make the system more robust to the breathing motion. This semi rigid fitting is limited in rotation, translation, and/or scale by any amount. For example, the rotation is limited to $+/-\pi/16$, the translation is limited to $+/-30$ pixels, and the scale is limited to 0.95-1.05. The same approach and/or limits are used for other medical devices and/or anatomy.

Figure 7:
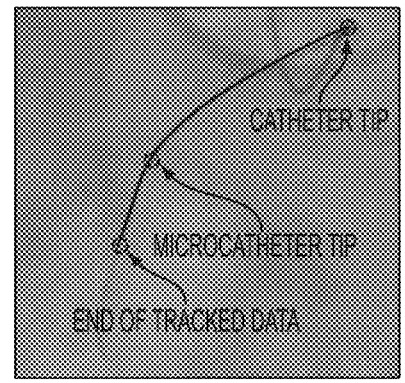
FIG. 7 illustrates example points used in fitting an angiography shape model to a fluoroscopy shape model.
Figure 8A:
FIGS. 8A and 8B show example fitting without weights and with weights, respectively.
Figure 8B:
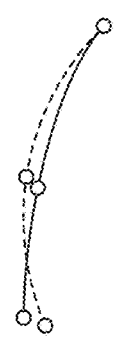

In another approach, key points along the guidewire are prioritized. These key points are less affected by the breathing motion. Any key points may be used. FIG. 7 shows one example of key points—catheter tip, microcatheter tip, and an end or last location of the medical device being tracked or detected. By increasing the weight of these key points in the fitting, the rotation factor may effectively be reduced. FIG. 8A shows fitting without weights, and FIG. 8B shows fitting with weights increased for the circular regions. This example fitting is of the medical device in angiography to the medical device in fluoroscopy.

Where the frames of the angiographic sequence are aligned to particular phases, the frames of fluoroscopic data at those phases are used. Alternatively, the fluoroscopic and/or angiographic frames are temporally interpolated to represent the same or similar phases. In one embodiment, each of the cardiac cycles from angiography providing a view of the coronary vessels is a source of one candidate overlay. Given a frame from fluoroscopy, the heart cycle phase is estimated or identified from EKG data. By taking the two closest frames bounding a similar heart cycle phase in each cycle of angiographic data, the pair of shape models are fit to the fluoroscopy frame's shape model, creating two overlays. The overlay with the least mean square error during the fitting is kept. By repeating this process for each cycle, one overlay per cycle is created as a candidate.

Figure 9:
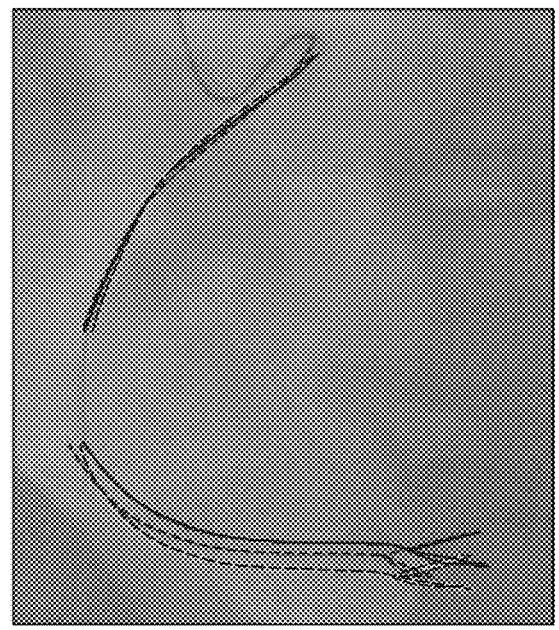
FIG. 9 shows example overlay candidates from angiography in a fluoroscopy image.

FIG. 9 show three example candidates. Each candidate is a fit of the model of the locations of the medical device from a different cycle of the angiography sequence to a model of the locations of the medical device in a frame of fluoroscopy data. The three overlay candidates from different source cycles are shown on a fluoroscopy image.

To create the final overlay to use, the candidates are combined. Alternatively, one of the candidates is selected using any criteria. For combination, two or more candidates are spatially combined.

Figure 10:
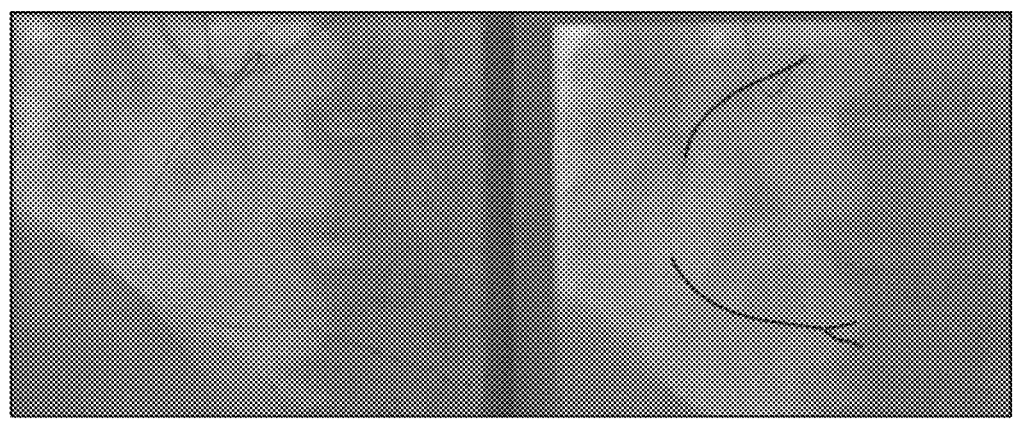
FIG. 10 shows an example angiograph image and a corresponding example fluoroscopy image with an overlay.

In one embodiment, the combination is by the processor averaging the fit shape models (i.e., averaging the candidates). This naive approach averages the candidates, such as interpolating point by point along the modeled locations. The averaging may create a visually smooth and natural appearance. FIG. 10 shows the result obtained from averaging where the left side is one angiography image and the right side is a fluoroscopy image with an overlay created by averaging the candidates from different cycles.

Figure 11:
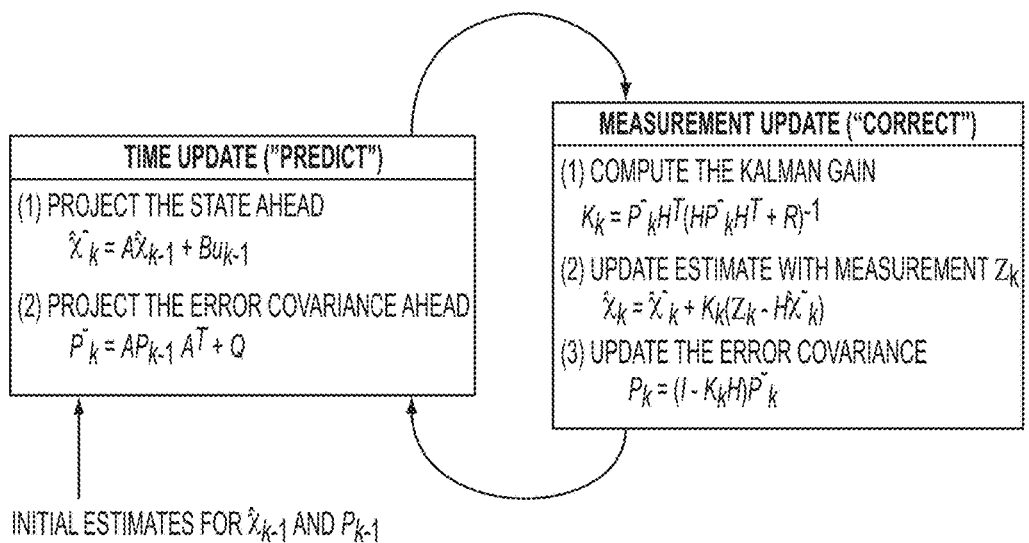
FIG. 11 represents a Kalman filtering combination.

In another embodiment, the combination is by Kalman filtering. The processor implements a Kalman filter. The candidate shape models or locations of the medical device and/or anatomy are used as noisy measurements in the Kalman filter. The Kalman filter uses noisy measurements and a prediction model to generate a prediction of the future state of a system. In other terms, the Kalman filter dynamically re-weights each measurement source to predict the next state while providing smooth results. FIG. 11 represents the Kalman filtering.

In act 40, the combination may be improved by using a prediction of the shape model or locations. The shape model before fitting, fitted candidate shape model, or combined shape model represents the anatomy and/or device at a given phase. The anatomy and/or device shape or locations for a temporally adjacent or other phase may be predicted from the information at the current phase. For example, motion between phases in angiography may be used to predict motion and resulting location in the other phase for fluoroscopy. As another example, motion between phases in angiography or fluoroscopy may be used to predict further motion between other phases in the same angiography or fluoroscopy. The combination then uses the prediction as a further factor in determining the final overlay position and shape. By using the prediction and based on the current position of the vessel, the future position of the vessel may be predicted. This prediction model may be used to generate one additional overlay candidate for a given phase.

Figure 12:
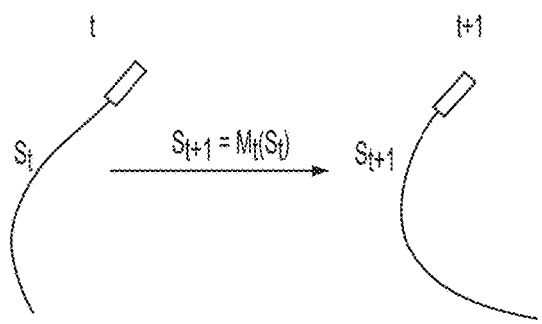
FIG. 12 represents motion between two shape models.

In one embodiment, the prediction uses the locations from the frames of angiography data. The motion of the catheter and of the coronary vessels is estimated in angiography. For prediction, the motion between phases is modeled. The shape models between two frames of angiography data are used to estimate their motion. The estimation is the motion $M_t$ of the spline $S_t$ modeling the catheter in both angiography and fluoroscopy from the frame t to the frame t+1, as represented in FIG. 12. Other devices or anatomy may be used to create the motion model.

Any motion model may be used, such as a linear model. The motion model may be expressed as:

$$X_t = \begin{matrix} x_1 \\ x_2 \end{matrix}, \quad (2)$$

$$X_{t+1} = \begin{matrix} y_1 \\ y_2 \end{matrix}$$

$$X_{t+1} = \begin{bmatrix} a_{11} & a_{12} \\ a_{21} & a_{22} \end{bmatrix} X_t + \begin{matrix} b_1 \\ b_2 \end{matrix}$$

Where a and b are translation and rotation parameters for the motion transform, and where $X_{t+1}$ is the point $X_t$ at t+1.

In order to estimate the parameters of this linear model, a set of correspondences from two adjacent frames of angiography data is used. The correspondences are used to scale the frames to each other and discretize the shape models. The catheter and vessel shape models constitute the initial set of points present in an angiography image. To re-sample this set of points for scaling, at least two points that have correspondences across different frames and corresponding phases are used, along with the shape model, to interpolate more points. Using the cubic spline, expressed as $\{y_x(t), y_y(t)\}$, the catheter tip and the micro-catheter tip are assumed as stationary in the vessel from one phase (e.g., frame) to another. After estimating the splines' parameters for each frame, correspondences are created by uniformly sampling points along the catheter splines with an equal distance d. The two stationary points can be used to identify a scaling factor.

Figure 13:
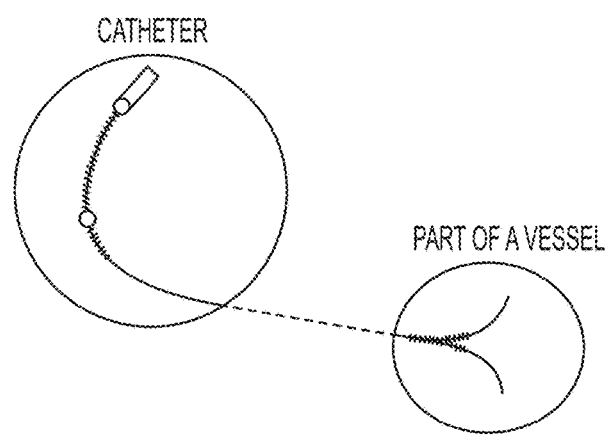
FIG. 13 represents discrete partitioning of a shape model.

The same approach may be used to generate more correspondences on the distal part of the catheter and on the vessel to make the model estimation more fitted to the motion around the vessel. The sampling to discretize the shape model (e.g., cubic spline) extends beyond one or more of the points used for scaling. FIG. 13 shows the points used for scaling as circles with the discrete sample points along the model as hash lines. The model or models are partitioned into samples for use in motion and/or combination.

Once scaled and sampled, the motion is estimated. Correlation, pattern matching, or other motion tracking may be used. In one embodiment, the linear transformation between the correspondences is determined. For example, the transform is represented as:

$$\begin{matrix} y_1 \\ y_2 \end{matrix} = \begin{bmatrix} a_{11} & a_{12} & b_1 \\ a_{21} & a_{22} & b_2 \end{bmatrix} \cdot \begin{bmatrix} x_1 \\ x_2 \\ 1 \end{bmatrix} \quad (3)$$

The form shown in equation (3) may be solved using Moore-Penrose's pseudoinverse or other approach to find the transformation matrix. Note that the set of points $X_t$ and $X_{t+1}$ may not always have the same size since a vessel might appear or disappear between two frames. Points along the vessels in one frame may be only considered when their correspondences are available in the other frame.

Using the frames of angiography data interpolated to common phases through the multiple cycles, inter-phase motion is obtained for prediction. Once each frame from the angiography sequence is registered to a phase, the motion between each pair of temporally adjacent phases is determined. Forward and/or reverse direction in time may be used. $T_{n-1}$ transformations are found, representing the motion between different pairs of frames. Since the motion is cyclical, a last transformation is provided between the last and first phase of a cycle, resulting in $T_n$ transformations for the $P_n$ phases.

The motion models or transformations may be refined. For example, a position of a model at one phase may be predicted from forward and reverse directions. The preceding and post phases are used to predict at the center phase. Given the two predictions of the location from the motion transforms, a final prediction may be created by interpolating between the two predictions.

For example, in order to predict the position of the catheter in the next frame of the angiography, the current position and a motion model are used. When these requirements are met, the prediction is performed using equation 2. For an angiography frame, two motion models may be obtained for the two bounding heart cycle phases. By using these two motions models on the shape models of the catheter and the vessels associated with the angiography frame, two predictions are obtained. A final prediction may be computed by interpolation. This approach may be represented as:

Function Estimate (k)
$P_k$←get phase (k)
$P_1$←$\lfloor P_k \rfloor$
$P_2$←$\lceil P_k \rceil$
$M_1$←get motion ($P_1$)
$M_2$←get motion ($P_2$)
$F_k$←get frame (k)
$F_1$←$M_1$ ($F_k$)
$F_2$←$M_2$ ($F_k$)
Return $F_2 \times ((P_k-P_1)/(P_2-P_1))+F_1 \times ((P_2-P_k)/(P_2-P_1))$ An angiography sequence is used to learn the motion models during one or more heart cycles. The motion model is then used to predict for the anatomy and/or the device. The prediction of act 40 is used in the combination of act 38. For example, the model motion is used to predict the locations in a different phase of an average from a combination in another phase. As another example, a Kalman filtering operation indicates a current location, and the motion model is used to predict a location in a next phase as part of Kalman filtering.

In the averaging combination example, the candidate locations for a given phase represented by a given fluoroscopic image are the fitted candidates from the same phase in different cycles of angiographic information and a prediction from one or more temporally adjacent phases. The prediction is based on the averaged result for that adjacent phase. The average is of the anatomy detected in the same phase from different cycles and a prediction for that same phase made from an average resulting from a different phase. For example, the prediction of the location of the anatomy in the fluoroscopy image is made from the motion estimate between the first phase and the second phase. The motion estimate is based on the detected anatomy. That motion estimate is used to predict the location of the average location of the anatomy in fluoroscopy from one phase to another.

In one embodiment, N+1 overlay candidates are fused to obtain only one final overlay. N is the number of cardiac cycles of available angiographic data at the same phase. The "+1" is a prediction of the location of the overlay from final overlay of a different phase using the motion model.

The N candidates may be substantially heterogeneous if bad fitting results are observed for the different candidates, such as due to breathing motion. The averaging, including a prediction, may overcome the bad fitting. Use of the Kalman filter may likewise overcome the bad fitting.

In the Kalman filter approach for combining, the prediction is included in the predictive stage of the Kalman filtering. The fitted candidate locations based on the angiograph shape models from different cycles for the same phase are used as noisy measurements. The prediction based on the final overlay from a different phase is used as the prediction of the locations in the prediction model of the Kalman filter. Alternatively, the predicted location is of the next phase from the Kalman combination of the noisy measurements.

The Kalman process is governed by:

$$x_k = Ax_{k-1} + Bu_{k-1} + w_{k-1}$$

$$z_k = Hx_k + v_k \qquad (4)$$

and:

$$p(w) \sim N(0,Q), p(v) \sim N(0,R) \qquad (5).$$

where $x_k$ is the state of the system at a time k, $x_{k-1}$ is the state at a time k−1 and the matrix A is a linear transformation that projects a state into its future state. The prediction is used in the linear transformation. The expression $Bu_{k-1}$ represents a controlled input and $w_{k-1}$ and $v_k$ are white noises with normal probabilities (represented in equation 5). The actual measurement of a state $x_k$ is denoted $z_k$, and the matrix H is the conversion between a state and its measurement. In the angiography to fluoroscopy overlay creation, a state is a frame of fluoroscopy data or the measurement is used directly ($z_k = x_k$ and $z_k = Hx_k$), and a measurement is an overlay or shape model. The motion of the catheter is determined to predict a future state from a current one. Because the input is not controlled, $Bu_{k-1}$ can be omitted and H is the identity matrix. The previously generated overlay candidates act as measurements in this model. The Kalman filter process happens in two steps: a prediction is made before being updated based on the measurements. The prediction is from the motion model. FIG. 11 shows the flow of this process. The result is a location of the anatomy and/or device for a given phase of a given fluoroscopy image using the candidates from angiography and the prediction.

Using the averaging, Kalman filtering, or other combination, a location combined from different candidates with or without the use of prediction from or to a different phase is provided as the overlay for the fluoroscopy image. The overlay may be for the anatomy and/or the device.

Referring again to FIG. 3, the overlay is visually generated in act 42. The overlay is of the anatomy and/or medical device. In one embodiment, the medical device is used for the prediction model, scaling, and other functions while the shape model for the anatomy is used for the overlay. Since the fluoroscopy image may not show the anatomy well, the overlay for the anatomy is added to the image. The positions or shape of the overlay is determined from the output combination of acts 38 and/or 40. The overlay is a function of the shapes of the anatomy determined from the angiographic images.

The overlay is a graphic on the image. The graphic is generated as a curve or sample points. In other embodiments, the graphic is generated by coloring pixels and/or changing brightness of pixels. The overlay highlights a portion of the image relative to other portions. The right side of FIG. 10 shows the overlay as a thick or bolded curve graphic added to the fluoroscopic image. In this embodiment, the overlay is displayed only for the samples on the vessel or of anatomy. The catheter or other devices are includes as part of the fluoroscopic image without additional highlighting or segmentation. Alternatively, the overlay includes or is only for the medical devices.

During an intervention, a sequence of fluoroscopy images is generated to guide or assist. The overlay is provided in each fluoroscopy image. As the images correspond to different phases, the combination is repeated for each new image. The motion model and angiographic shape models may be the same, but the fitting of candidates, prediction, and combination are performed to find the location of the overlay in each newly acquired frame of fluoroscopy data. The overlay of the vessel is generated in real-time for each of a sequence of fluoroscopy images during an intervention, such as a catheter intervention.

In one embodiment, a catheter in fluoroscopy is tracked via angiography. Injecting contrast agent, other than for the initial sequence of angiography, for tracking may be avoided. A dynamic overlay of the coronary vessels over the fluoroscopy x-ray images in real time is provided. This overlay is based on tracking the vessels in the angiography sequence during only a few cardiac cycles following the first contrast injection. By estimating the motion of the catheter and of the vessels during the procedure, a model to predict their position in future frames is created. Candidate overlays from the angiography sequence are generated and fused to create a final overlay. The dynamic overlay may help the practitioner visualize the coronary vessels in real time without injection of any more contrast injection.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for generating an overlay of anatomy in a fluoroscopy image, the method comprising:
   acquiring, with an angiograph, an angiograph image representing the anatomy of a patient at a first phase of a first cardiac cycle of the patient;
   acquiring, with a fluoroscope, a fluoroscopic image representing the anatomy of the patient at a first phase of a second cardiac cycle of the patient;
   determining, by a processor, a shape of the anatomy in the fluoroscopic image from the angiograph image; and
   generating the overlay of the anatomy as a graphic on the fluoroscopic image, the overlay being a function of the shape determined from the angiograph image.

2. The method of claim 1 wherein acquiring the angiograph image comprises obtaining a first frame of data representing the anatomy and a catheter, and wherein acquiring the fluoroscopic image comprises obtaining a second frame of data representing the anatomy and the catheter.

3. The method of claim 1 wherein acquiring the angiograph image comprises acquiring the angiograph image and a plurality of other angiograph images in a first multi-heart cycle series with first EKG timing information for each of the angiograph images.

4. The method of claim 3 wherein determining comprises:
   fitting at least two shape models of the anatomy from at least two angiograph images of a same phase from different cycles to the fluoroscopic image of the same phase, and
   combining the at least two fit shape models as the overlay.

5. The method of claim 4 wherein combining comprises averaging the at least two fit shape models.

6. The method of claim 4 wherein combining comprises applying a Kalman filter with the at least two fit shape models as noisy measurements.

7. The method of claim 6 further comprising predicting a first prediction of the shape of the anatomy from a different phase, wherein applying the Kalman filter comprises using the first prediction of the shape as a prediction model in the Kalman filter.

8. The method of claim 3 wherein acquiring the fluoroscope image comprises acquiring the fluoroscope image and a plurality of other fluoroscope images over at least one heart cycle with second EKG timing information for each of the fluoroscope images, where the acquiring of the fluoroscope images is unsynchronized with the acquiring of the angiograph images; and
   further comprising interpolating the angiograph images from different heart cycles to common phases.

9. The method of claim 1 wherein determining comprises determining the shape as a function of a first prediction of the shape from a second phase of the first cardiac cycle to the first phase of the first cardiac cycle.

10. The method of claim 9 further comprising predicting the first prediction of the shape from a motion estimate of the anatomy between the first phase of the first cardiac cycle and the second phase of the first cardiac cycle.

11. The method of claim 10 wherein predicting comprises predicting a second prediction of the shape in the second phase of the first cardiac cycle from another motion estimate of the anatomy between a third phase of the first cardiac cycle and the second phase of the first cardiac cycle, and
   further comprising interpolating the shape from the first and second predictions of the shape.

12. The method of claim 10 wherein predicting comprises predicting the first prediction of the shape from an average of the anatomy detected in the second phase in different cardiac cycles, and wherein determining further comprises averaging the anatomy detected in the first phases from the different cardiac cycles and the first prediction of the shape.

13. The method of claim 1 wherein generating the overlay comprises highlighting the anatomy on the fluoroscopic image.

14. The method of claim 1 wherein generating the overlay comprises generating the overlay of a vessel in real-time for each of a sequence of fluoroscopy images during a catheter intervention.

* * * * *